(12) United States Patent
Migita et al.

(10) Patent No.: US 9,198,611 B2
(45) Date of Patent: Dec. 1, 2015

(54) INFORMATION PROCESSING DEVICE, IMAGE OUTPUT METHOD, AND PROGRAM

(75) Inventors: Takahito Migita, Tokyo (JP); Naoki Kamimaeda, Kanagawa (JP); Takuya Nishimura, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 13/071,789

(22) Filed: Mar. 25, 2011

(65) Prior Publication Data

US 2011/0246509 A1 Oct. 6, 2011

(30) Foreign Application Priority Data

Mar. 30, 2010 (JP) .................. P2010-078892

(51) Int. Cl.
*A63B 71/00* (2006.01)
*A61B 5/22* (2006.01)
*A61B 5/00* (2006.01)
*A63B 24/00* (2006.01)
*G06K 9/00* (2006.01)

(52) U.S. Cl.
CPC .................. *A61B 5/222* (2013.01); *A61B 5/744* (2013.01); *A63B 24/0062* (2013.01); *A63B 24/0084* (2013.01); *A63B 24/0087* (2013.01); *G06K 9/00335* (2013.01); *A63B 2024/0068* (2013.01); *A63B 2024/0096* (2013.01)

(58) Field of Classification Search
CPC ........... A63B 24/0062; A63B 24/0084; A63B 2024/0068
USPC .......................................................... 482/9
See application file for complete search history.

(56) References Cited

U.S. PATENT DOCUMENTS

| | | | | |
|---|---|---|---|---|
| 5,213,555 A | * | 5/1993 | Hood et al. | 482/57 |
| 6,050,924 A | * | 4/2000 | Shea | 482/57 |
| 7,761,300 B2 | * | 7/2010 | Klingler | 704/260 |
| 7,967,731 B2 | * | 6/2011 | Kil | 482/8 |
| 8,620,146 B1 | * | 12/2013 | Coleman | 386/278 |
| 2005/0192156 A1 | * | 9/2005 | Daikeler et al. | 482/9 |
| 2005/0236004 A1 | * | 10/2005 | Magnuson et al. | 128/898 |
| 2006/0074279 A1 | * | 4/2006 | Brover | 600/300 |
| 2008/0125289 A1 | * | 5/2008 | Pryor et al. | 482/8 |
| 2009/0029769 A1 | * | 1/2009 | Muller | 463/31 |
| 2010/0004097 A1 | * | 1/2010 | D'Eredita | 482/8 |
| 2010/0210418 A1 | * | 8/2010 | Park | 482/8 |
| 2010/0222179 A1 | * | 9/2010 | Temple et al. | 482/8 |
| 2011/0092337 A1 | * | 4/2011 | Srinivasan et al. | 482/8 |

FOREIGN PATENT DOCUMENTS

| | | |
|---|---|---|
| JP | 08-128219 | 5/1996 |
| JP | 10-113343 | 5/1998 |
| JP | 2002-210060 | 7/2002 |

(Continued)

*Primary Examiner* — Cheyne D Ly
(74) *Attorney, Agent, or Firm* — Wolf, Greenfield & Sacks, P.C.

(57) ABSTRACT

There is provided an information processing device including: a storage unit that stores a plurality of exercise models each including one or more kinds of measured values measured in time series for a person doing exercise and exercise description data specifying exercise recognized based on the measured values; a selection unit that selects one or more exercise models from the plurality of exercise models stored in the storage unit according to a designated condition; and an output unit that outputs a series of output images representing the measured values and exercise specified by the exercise description data in time series for the exercise model selected by the selection unit.

24 Claims, 17 Drawing Sheets

DISTANCE D1 TO PERSON IN EXERCISE MODEL (TIME t1)

DISTANCE D2 TO PERSON IN EXERCISE MODEL (TIME t2)
(D2 > D1)

(56) References Cited

FOREIGN PATENT DOCUMENTS

| JP | 2002 291952 | 10/2002 |
| JP | 2002-346013 | 12/2002 |
| JP | 2003-205051 | 7/2003 |
| JP | 2004-532699 | 10/2004 |
| JP | 2010-067002 | 3/2010 |
| KR | WO 2009/051316 | * 6/2009 ............ A63B 22/02 |

* cited by examiner

FIG.9

SELECTION CONDITION DESIGNATION SCREEN — W2

- NUMBER OF MODELS: 3 — F21
- TARGET PERIOD: PAST ONE WEEK — F22
- TYPE — F23
  - NOT SPECIFIED
  - YOU
  - ANOTHER USER
  - WELL-KNOWN PERSON
  - PERSON A
  - ..
- ADDITIONAL CONDITION: AGE — F24

INFORMATION PROCESSING DEVICE, IMAGE OUTPUT METHOD, AND PROGRAM

BACKGROUND OF THE INVENTION

1. Field of the Invention

The present invention relates to an information processing device, an image output method, and a program.

2. Description of the Related Art

Physical exercises aiming to maintain or improve health, enhance athletic ability and so on are performed on a routine basis today. Jogging, walking, cycling, swimming or the like is among examples of such physical exercises. As techniques to support exercise of a user, there are techniques to measure biometric information of a user doing exercise, techniques to manage measured information, techniques to recommend some type of exercise to a user and so on. For example, Japanese Unexamined Patent Application Publication No. 2002-291952 discloses a technique that delivers exercise program data indicating the content of exercise recommended based on physical data of a user from a server to a wrist watch of the user, so that even a person with no expert knowledge on exercise can do appropriate exercise.

SUMMARY OF THE INVENTION

However, the technique disclosed in Japanese Unexamined Patent Application Publication No. 2002-291952 merely presents the content of exercise and the duration or the number of times of exercise which are specified in the exercise program data to a user on a screen of a wrist watch. Thus, the technique may not allow a user for comparing between the present and past exercises of the user or comparing between exercise of the user and exercise of another user. Further, there seems to be no technique that allows a user to easily make the above-described comparison of exercise while doing exercise.

In light of the foregoing, it is desirable to provide novel and improved information processing device, image output method and program that allow a user to easily recognize exercise for comparison while doing exercise.

According to an embodiment of the present invention, there is provided an information processing device including: a storage unit that stores a plurality of exercise models each including one or more kinds of measured values measured in time series for a person doing exercise and exercise description data specifying exercise recognized based on the measured values; a selection unit that selects one or more exercise models from the plurality of exercise models stored in the storage unit according to a designated condition; and an output unit that outputs a series of output images representing the measured values and exercise specified by the exercise description data in time series for the exercise model selected by the selection unit.

The output image may be an image displaying a character as an avatar of a person doing exercise specified by the exercise description data.

The output unit may vary a state of the character in time series according to the measured values in the selected exercise model.

The exercise model may include position data indicating a position of a person doing exercise, the information processing device may further include a position acquisition unit that acquires a current position of a user, and the output unit may vary a display position or a size of the character in time series according to the position of the person indicated by the position data of the selected exercise model and the current position of the user acquired by the position acquisition unit.

The output image may be an image further displaying at least one kind of the measured values.

A condition for selecting an exercise model of a person being the same as a user doing exercise may be included as an option of the condition.

A condition for selecting an exercise model of a well-known person may be included as an option of the condition.

A condition for selecting an exercise model of a person with at least one attribute of age, sex, height and weight being common or similar to a user doing exercise may be included as an option of the condition.

The information processing device may further include: a measurement unit that outputs the one or more kinds of measured values for a user doing exercise; and an exercise recognition unit that recognizes exercise of a user based on the measured values output by the measurement unit, wherein when current exercise of the user recognized by the exercise recognition unit is different from exercise specified by the exercise description data of the exercise model being processed by the output unit, the selection unit may select another exercise model to be processed by the output unit.

The information processing device may further include: a measurement unit that outputs the one or more kinds of measured values for a user doing exercise; an exercise recognition unit that recognizes exercise of a user based on the measured values output by the measurement unit; and an exercise model creation unit that creates the exercise model for the user using a recognition result by the exercise recognition unit.

According to another embodiment of the present invention, there is provided an image output method using an information processing device including a storage unit that stores a plurality of exercise models each including one or more kinds of measured values measured in time series for a person doing exercise and exercise description data specifying exercise recognized based on the measured values, the method including steps of: selecting one or more exercise models from the plurality of exercise models stored in the storage unit according to a designated condition; and outputting a series of output images representing the measured values and exercise specified by the exercise description data in time series for the selected exercise model.

According to another embodiment of the present invention, there is provided a program causing a computer that controls an information processing device including a storage unit that stores a plurality of exercise models each including one or more kinds of measured values measured in time series for a person doing exercise and exercise description data specifying exercise recognized based on the measured values to function as: a selection unit that selects one or more exercise models from the plurality of exercise models stored in the storage unit according to a designated condition; and an output unit that outputs a series of output images representing the measured values and exercise specified by the exercise description data in time series for the exercise model selected by the selection unit.

According to the embodiments of the present invention described above, it is possible to provide the information processing device, image output method and program that allow a user to easily recognize exercise for comparison while doing exercise.

BRIEF DESCRIPTION OF THE DRAWINGS

FIG. 9 is an explanatory view to explain a selection condition designation screen according to one embodiment;

DETAILED DESCRIPTION OF THE EMBODIMENT(S)

Figure 1:
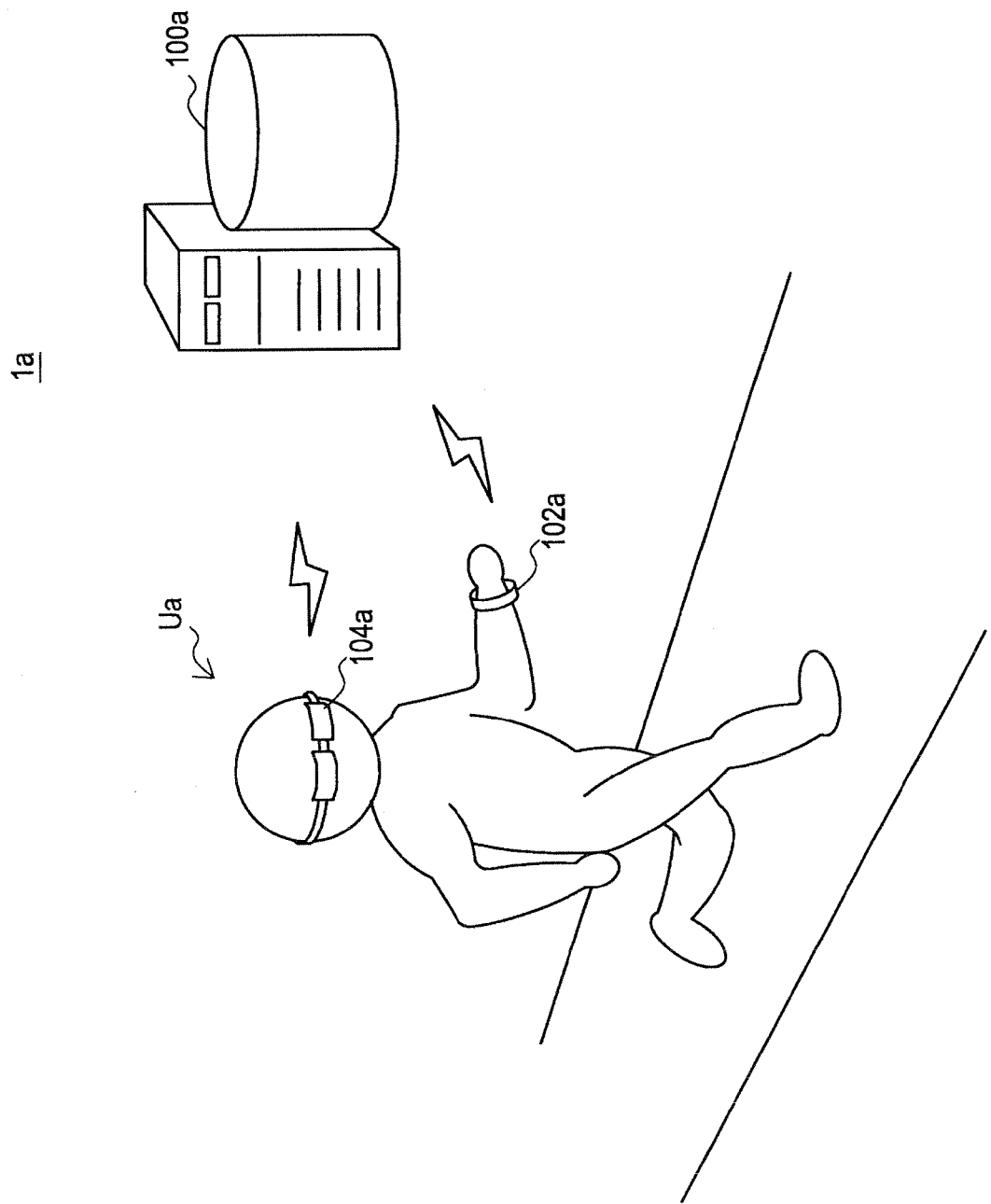
FIG. 1 is a first schematic view showing an overview of an information processing system according to one embodiment.

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

Preferred embodiments of the present invention will be described hereinafter in the following order.

1. Overview of System
2. Configuration of Information Processing Device according to Embodiment
2-1. Registration of User Data
2-2. Measurement and Recognition of Exercise
2-3. Creation of Exercise Model
2-4. Display of Exercise Model
3. Flow of Process according to Embodiment
3-1. Overall Flow
3-2. Model Creation Process
3-3. Model Display Process
4. Summary

1. OVERVIEW OF SYSTEM

An overview of an information processing system according to one embodiment of the present invention is described hereinafter with reference to FIGS. 1 to 3.

FIG. 1 is a schematic view showing an overview of an information processing system 1a according to one embodiment of the present invention. Referring to FIG. 1, a user Ua of the information processing system 1a is running. The information processing system 1a includes an information processing device 100a, a sensor set 102a, and a display device 104a.

The sensor set 102a is worn by the user Ua. While the user Ua is doing exercise, the sensor set 102a periodically acquires one or more kinds of measured values for the user Ua and transmits the acquired measured values to the information processing device 100a. FIG. 1 shows only the sensor set 102a which is worn on the wrist of the user for simplification of the figure. However, sensors included in the sensor set 102a may be worn on other parts of the body of a user or carried by a user. The sensor set 102a may include an acceleration sensor that acquires the acceleration of each part of the body of the user Ua, a gyro sensor that acquires the posture of each part, an myoelectric sensor that acquires the myoelectric potential of each part, a heart beat meter that acquires the heart beat of the user Ua, a respirometer that acquires the breathing rate, a clinical thermometer that acquires the body temperature, a sudorometer that acquires the sweating or the like.

The display device 104a is worn by the user Ua. The display device 104a receives an output image created by the information processing device 100a and displays the received output image for the user Ua. In the example of FIG. 1, the display device 104a is a head-mounted display.

The information processing device 100a is a device that processes the measured values received from the sensor set 102a and creates the output image to be displayed for the user Ua. The information processing device 100a may be a general-purpose computer having a connection interface (i.e. a wireless or wired communication interface) to make connection with the sensor set 102a and the display device 104a, for example. Further, it is not limited to the example of FIG. 1, and the information processing device 100a may be a device which is physically integral with any one or both of the sensor set 102a and the display device 104a.

Figure 2:
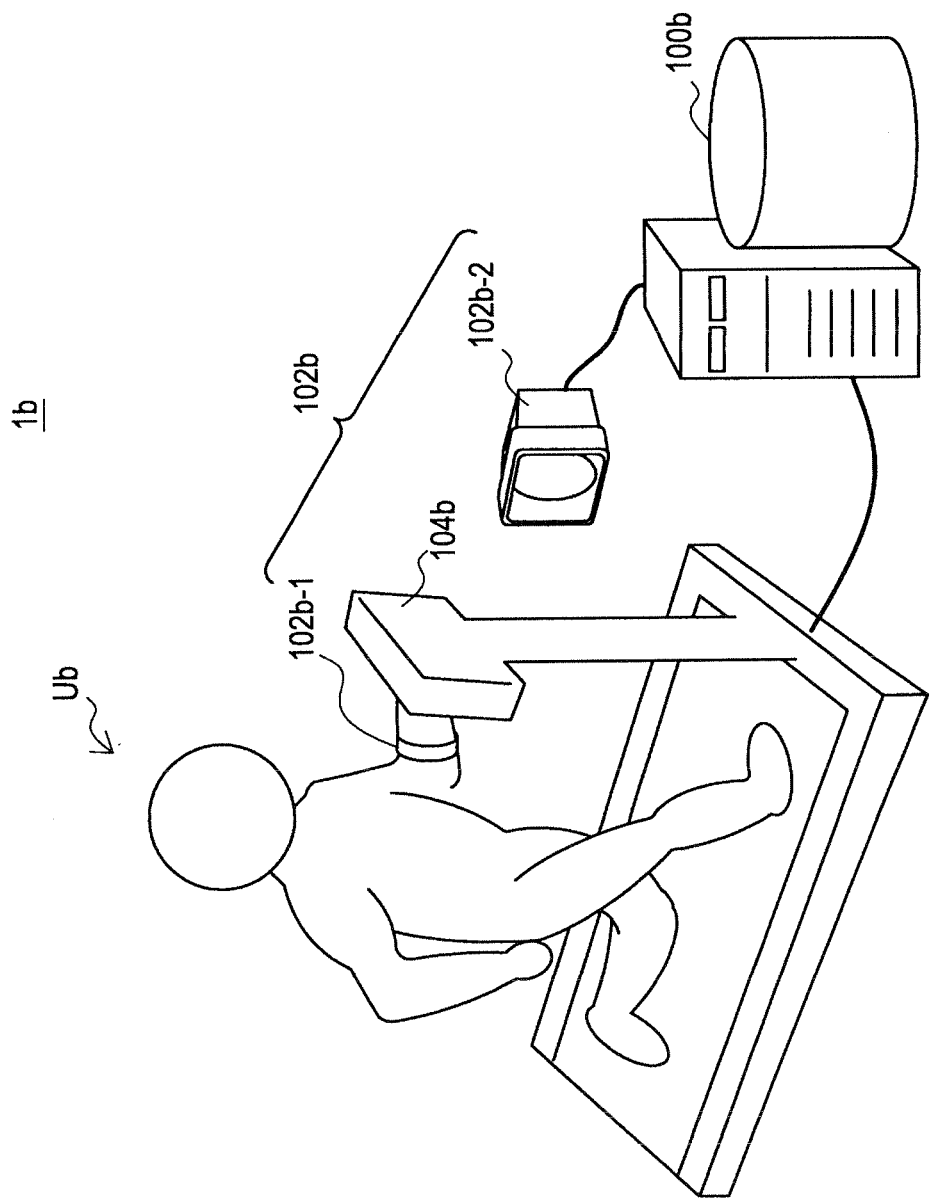
FIG. 2 is a second schematic view showing an overview of an information processing system according to one embodiment.

FIG. 2 is a schematic view showing an overview of an information processing system 1b according to another embodiment of the present invention. Referring to FIG. 2, a user Ub of the information processing system 1b is running on a treadmill. The information processing system 1b includes an information processing device 100b, a sensor set 102b, and a display device 104b.

Some sensor 102b-1 of the sensor set 102b is worn by the user Ub. On the other hand, other sensor 102b-2 of the sensor set 102b is not worn by the user Ub. While the user Ub is doing exercise, the sensor set 102b periodically acquires one or more kinds of measured values for the user Ub and transmits the acquired measured values to the information processing device 100b, just like the sensor set 102a of FIG. 1. The sensor 102b-1 which is worn by the user may include a sensor similar to that of the sensor set 102a of FIG. 1, such as an acceleration sensor that acquires the acceleration of each part of the body of the user Ub. Further, the sensor 102b-2 may include a clinical thermometer that acquires the body temperature of the user Ub by detecting infrared rays emitted from the body of the user Ub, a concentration meter that acquires the carbon dioxide levels of the expired air of the user Ub or the like.

The display device 104a is mounted on the treadmill being used by the user Ub. The display device 104a receives an output image created by the information processing device 100b and displays the received output image for the user Ub.

The information processing device 100b is a device that processes the measured values received from the sensor set 102b and creates the output image to be displayed for the user Ub, just like the information processing device 100a of FIG. 1. The information processing device 100b may be a general-purpose computer having a connection interface to make connection with the sensor set 102b and the display device 104b, for example. Further, it is not limited to the example of FIG. 2, and the information processing device 100b may be a device which is physically integral with any one or both of the sensor set 102b and the display device 104b.

Figure 3:
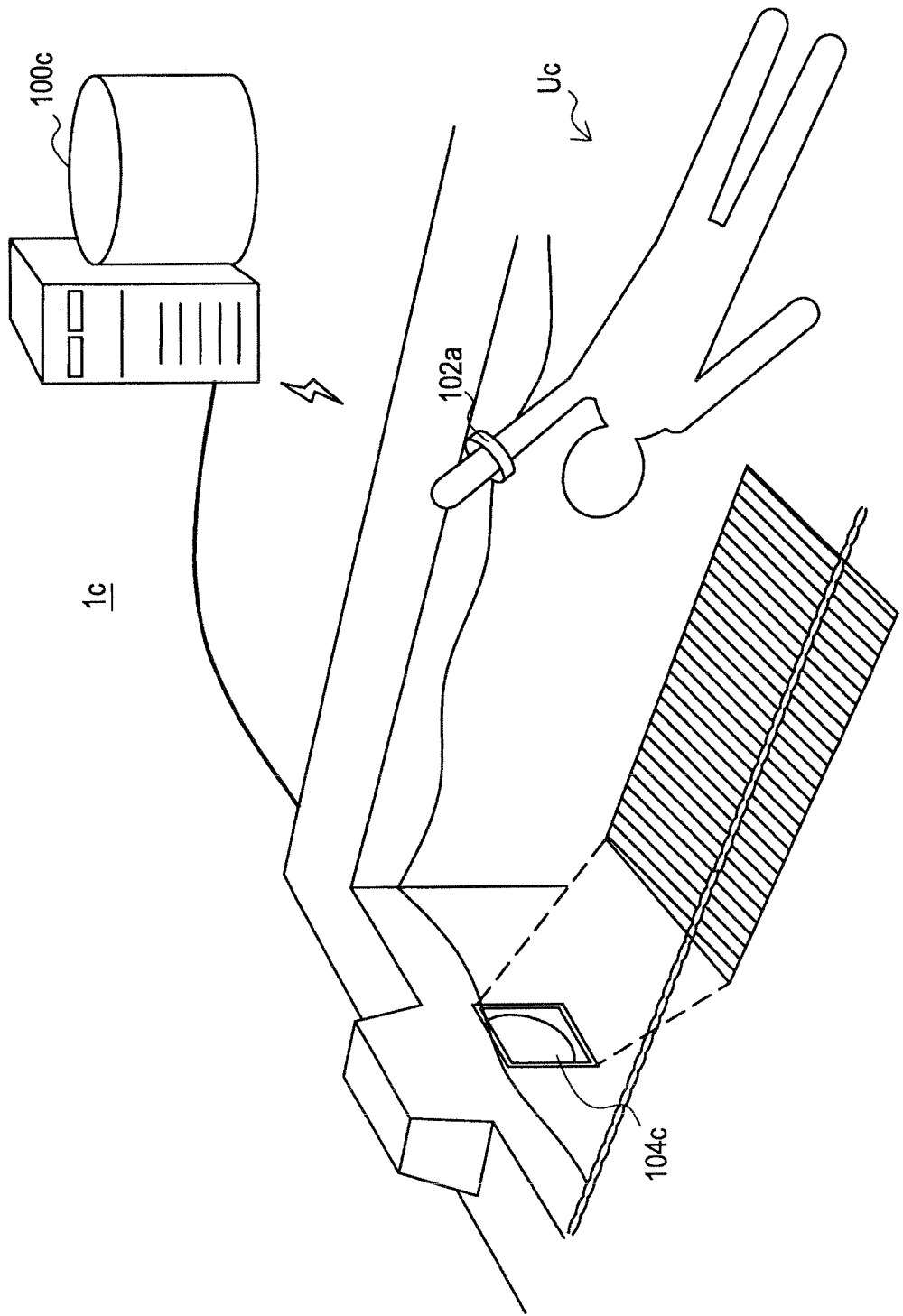
FIG. 3 is a third schematic view showing an overview of an information processing system according to one embodiment.

FIG. 3 is a schematic view showing an overview of an information processing system 1c according to yet another embodiment of the present invention. Referring to FIG. 3, a user Uc of the information processing system 1c is swimming in a swimming pool. The information processing system 1c includes an information processing device 100c, a sensor set 102a, and a display device 104c. The sensor set 102a is the same as the sensor set which is described earlier with reference to FIG. 1.

The display device 104c is a projector capable of projecting an image on the bottom surface of the swimming pool where the user Uc is swimming. The display device 104c receives an output image created by the information processing device 100c and projects the received output image on the bottom surface of the swimming pool. Note that, in the information processing system 1c, a screen of the display device may be mounted on the bottom surface of the swimming pool, rather than projecting an image on the bottom surface of the swimming pool using the projector.

The information processing device 100c is a device that processes the measured values received from the sensor set 102a and creates the output image to be projected by the display device 104c, just like the information processing device 100a of FIG. 1. The information processing device 100c may be a general-purpose computer having a connection interface to make connection with the sensor set 102a and the display device 104c, for example.

Thus, any of the information processing devices 100a to 100c described with reference to FIGS. 1 to 3 is a device that measures one or more kinds of measured values for a user doing exercise and creates an output image to be displayed for the user. In the following description of this specification, when there is no need to distinguish among the information processing devices 100a, 100b and 100c, they are collectively referred to as the information processing device 100 by omitting the alphabetical letter at the end of the symbol. The same applies to the information processing system 1 (1a, 1b and 1c), the sensor set 102 (102a and 102b), and the display device 104 (104a, 104b and 104c).

2. CONFIGURATION OF INFORMATION PROCESSING DEVICE ACCORDING TO EMBODIMENT

Figure 4:
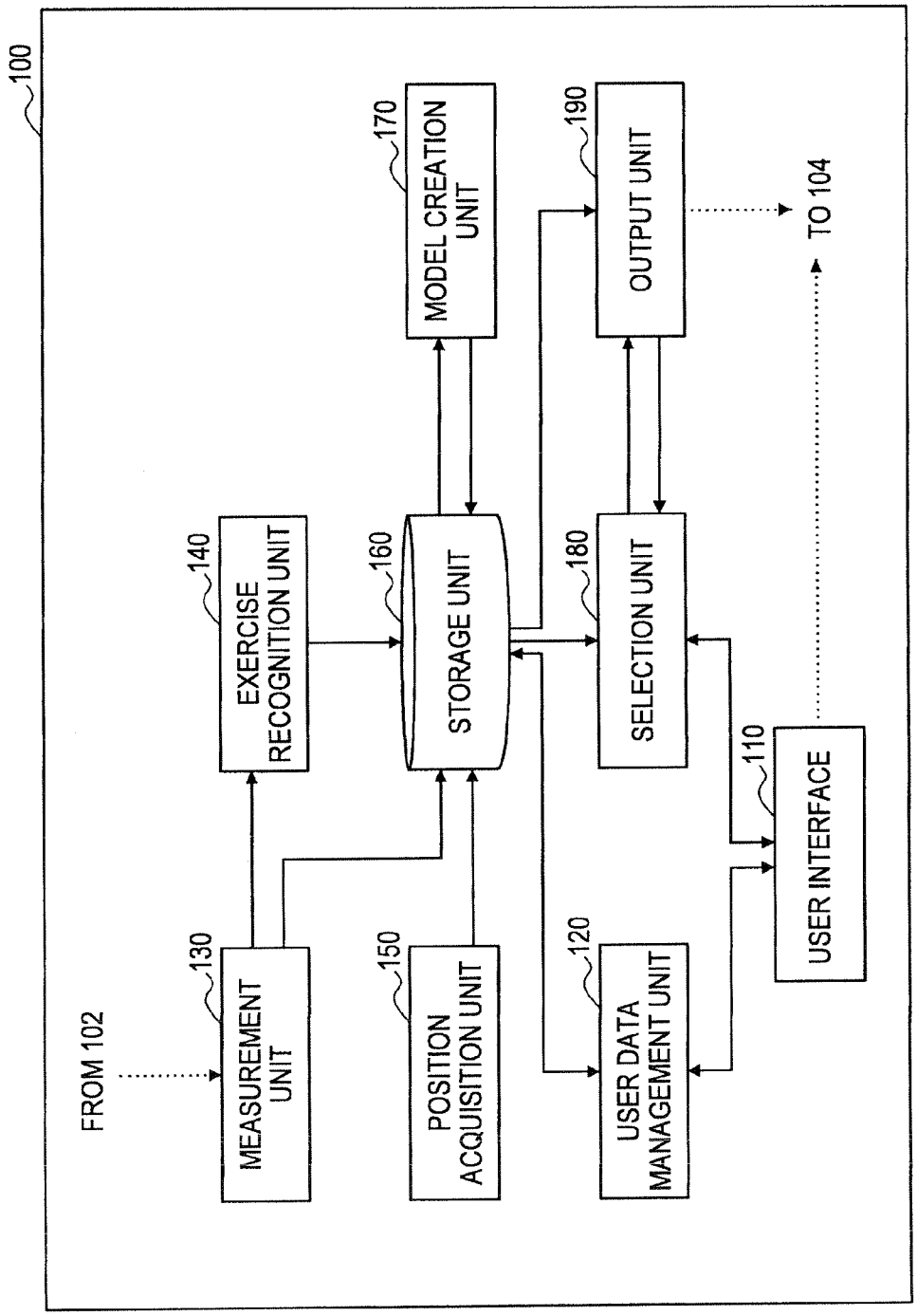
FIG. 4 is a block diagram showing an example of a configuration of an information processing device according to one embodiment.

A specific configuration of the information processing device 100 according to one embodiment of the present invention is described hereinafter with reference to FIGS. 4 to 14. FIG. 4 is a block diagram showing an example of the configuration of the information processing device 100 according to one embodiment, Referring to FIG. 4, the information processing device 100 includes a user interface 110, a user data management unit 120, a measurement unit 130, an exercise recognition unit 140, a position acquisition unit 150, a storage unit 160, a triode creation unit 170, a selection unit 180, and an output unit 190.

[2-1. Registration of User Data]

The user interface 110 provides an interface for the information processing device 100 to accept an instruction or information input from a user. The user interface 110 may be GUI (Graphical User Interface) using a screen displayed by the display device 104, or an audio input interface or the like. The user interface 110 is used not only for registration of user data, which is described in this section, but also for input of conditions when displaying an exercise model, which is described later.

The user data management unit 120 manages user data for a user of the information processing device 100. The user data is input by a user through a user data registration screen W1 as shown in FIG. 5, for example.

Figure 5:
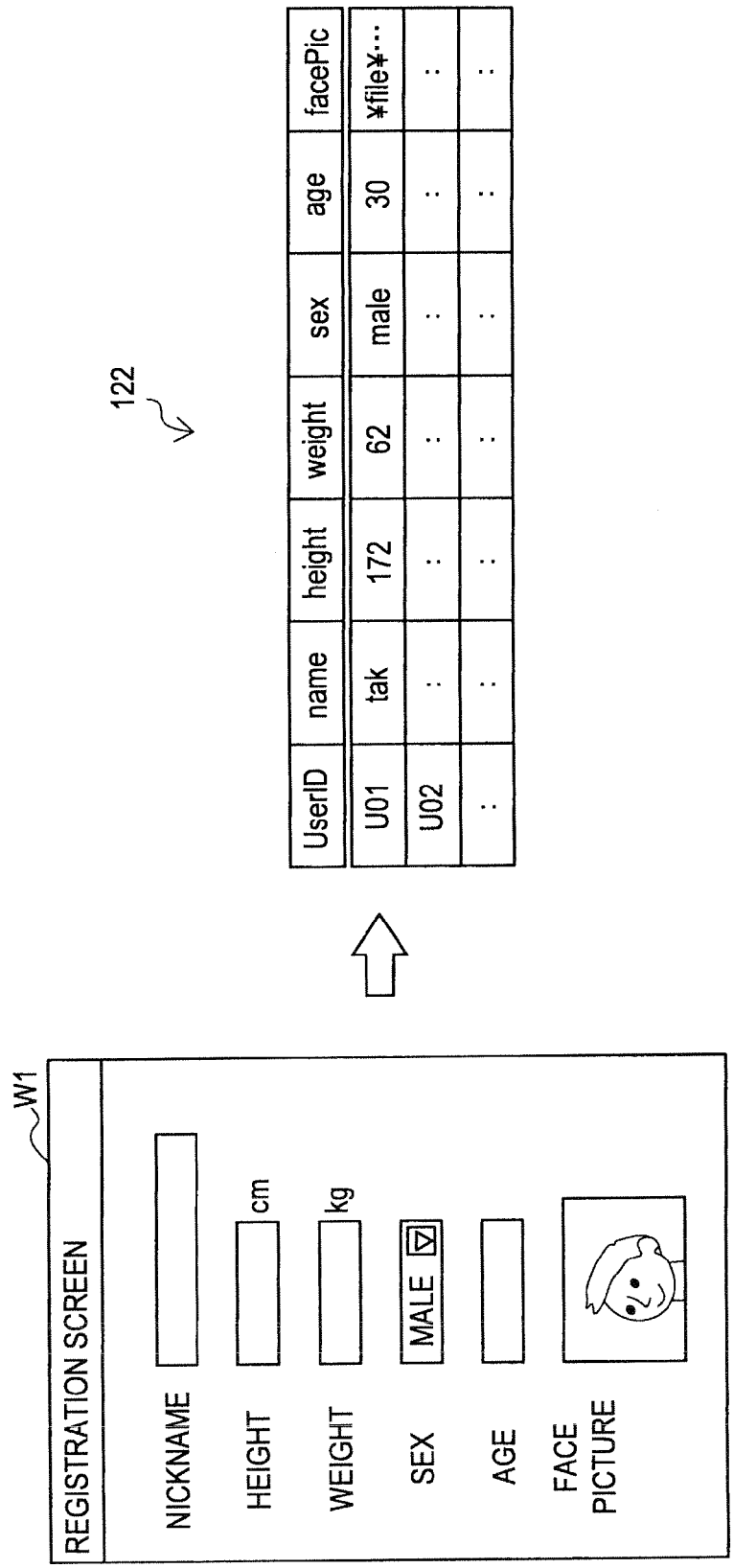
FIG. 5 is an explanatory view to explain registration of user data according to one embodiment.

Referring to FIG. 5, the user data registration screen W1 is shown at the left. The user data registration screen W1 contains an attribute input field for inputting a nickname, height, weight, sex and age of one user and a designation field for designating a face picture, for example. The user data management unit 120 acquires attribute values of each user through the user data registration screen W1 and stores user data containing the acquired attribute values into the storage unit 160.

User data 122 as an example stored in the storage unit 160 is shown at the right of FIG. 5. The user data 122 contains six attribute items of nickname (name), height, weight, sex, age and file pass (facePic) of an image file of a face picture in addition to a user ID for identifying each user. The attribute values for those attribute items may be updatable by a user using a user data update screen (not shown) provided by the user data management unit 120, for example.

[2-2. Measurement and Recognition of Exercise]

Processing by the information processing device 100 after the user data is registered is broadly divided into measurement and recognition of exercise, creation of exercise model, and display of exercise model. In this section, the measurement and recognition of exercise are described. The measurement and recognition of exercise mainly involve the measurement unit 130, the exercise recognition unit 140, the position acquisition unit 150 and the storage unit 160.

The measurement unit 130 measures one or more kinds of parameters for a user doing exercise with use of the sensor set 102 and outputs measured values as a result of the measurement to the exercise recognition unit 140 and the storage unit 160. The measured values output from the measurement unit 130 may be measured values for various parameters such as the acceleration and posture of parts (e.g. both hands, both feet, hip etc.) of the body of a user, and the heart beat and breathing rate of a user. The output of the measured values by the measurement unit 130 is typically performed periodically while the user is doing exercise. As a result, a time-series of measured values are output for a series of exercises by the user.

The exercise recognition unit 140 recognizes the user's exercise based on the measured values output from the measurement unit 130. The exercise recognition process by the exercise recognition unit 140 may be a process on the basis of HMM (Hidden Markov Model) as disclosed in Japanese Unexamined Patent Application Publication No. 2006-340903 and Japanese Unexamined Patent Application Publication No. 2009-118513, for example. In this case, the type of exercise by a user may be specified from candidates such as "walking", "running" and "resting" by using output values of the acceleration sensor and the posture sensor (gyro sensor). Further, the exercise recognition process by the exercise recognition unit 140 may be a process using a discriminant function which is obtained in advance by known supervised learning (e.g. learning on the basis of SVM (Support Vector Machine) or neural network etc.). In this case, using measured values output from the measurement unit 130 for exercise whose type of exercise is known, the discriminant function for identifying the type of exercise from the measured values is obtained by an advance learning process. Then, when new measured values are output from the measurement unit 130 for unknown exercise, the exercise recognition unit 140 applies the discriminant function obtained in advance to the new measured values.

Figure 6:
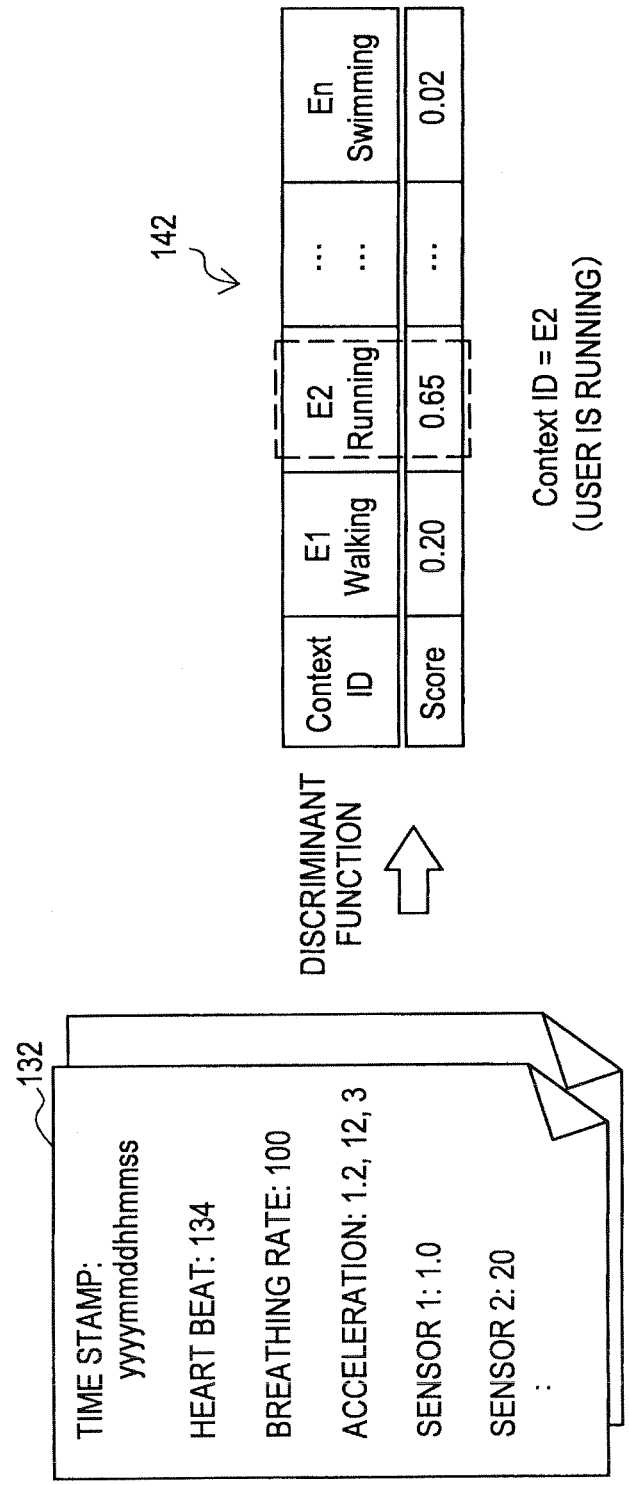
FIG. 6 is an explanatory view to explain an exercise recognition process according to one embodiment.

FIG. 6 is an explanatory view to explain an example of the exercise recognition process by the exercise recognition unit 140. Measured data 132 that contains a set of measured values which are periodically output from the measurement unit 130 is shown at the left of FIG. 6. The measured data 132 contains a time stamp indicating the time of measurement and measured values for one or more kinds of parameters (e.g. heart beat, breathing rate, three-axis acceleration etc.). The exercise recognition unit 140 applies the discriminant function obtained in advance to the measured data 132 to thereby calculate a score for each type of exercise. The data applied to the discriminant function may be one set of measured data 132 associated with one time stamp or a plurality of sets of measured data 132 over a given past period (several seconds etc.). The calculated score indicates the probability that exercise as a target of recognition is exercise of a type identified by each context ID (Context ID: Exercise ID). For example, at the right of FIG. 6, the score for context ID=E1 ("Walking") is 0.20, the score for context ID=E2 ("Running") is 0.65, and the score for context ID=En ("Swimming") is 0.02. In this case, for exercise as a target of recognition, it is recognized that the possibility that a user is running ("Running") is the highest. The exercise recognition unit 140 outputs such scores or the context ID specifying the type of exercise which is recognized as being most likely as exercise description data 142 to the storage unit 160.

The position acquisition unit 150 periodically acquires the current position of a user while the user is doing exercise. Then, the position acquisition unit 150 outputs position data indicating the acquired position to the storage unit 160. The position acquisition unit 150 may acquire the current position of a user by GPS (Global Positioning System) function, for example. Alternatively, the acquisition unit 150 may acquire the current position of a user by summation of a speed vector obtained by integrating the acceleration of a user measured by the measurement unit 130, for example.

It should be noted that, in the information processing system 1b described with reference to FIG. 2, a user does not move from the treadmill. In this case, a virtual movement of the user from the start of exercise is calculated by summation of a running speed output from a speed sensor mounted on the treadmill. Then, the position acquisition unit 150 acquires the position of the user (e.g. the displacement from the start point) in the virtual space according to the calculated virtual movement.

The storage unit 160 stores the measured data 132 input from the measurement unit 130, the exercise description data 142 input from the exercise recognition unit 140, and the position data input from the position acquisition unit 150 in a time series manner using hard disk or semiconductor memory. Using those data stored in the storage unit 160, an exercise model that models a series of exercises by a user is created.

[2-3. Creation of Exercise Model]

In this specification, the exercise model is model data that includes one or more kinds of measured values measured in time series for a person doing exercise (including a person being a user of the information processing system 1 and another person) and exercise description data specifying exercise of a person recognized based on the measured values. The creation of the exercise model mainly involves the storage unit 160 and the model creation unit 170.

The model creation unit 170 creates the exercise model using the recognition result by the exercise recognition unit 140 described above. The creation of the exercise model may be performed at the point of time when the measurement and recognition of exercise, which are described in the previous section, end for a series of exercises by a user, for example. Alternatively, the creation of the exercise model may be performed at regular periods for data accumulated in the storage unit 160 over a given period, for example.

Figure 7:
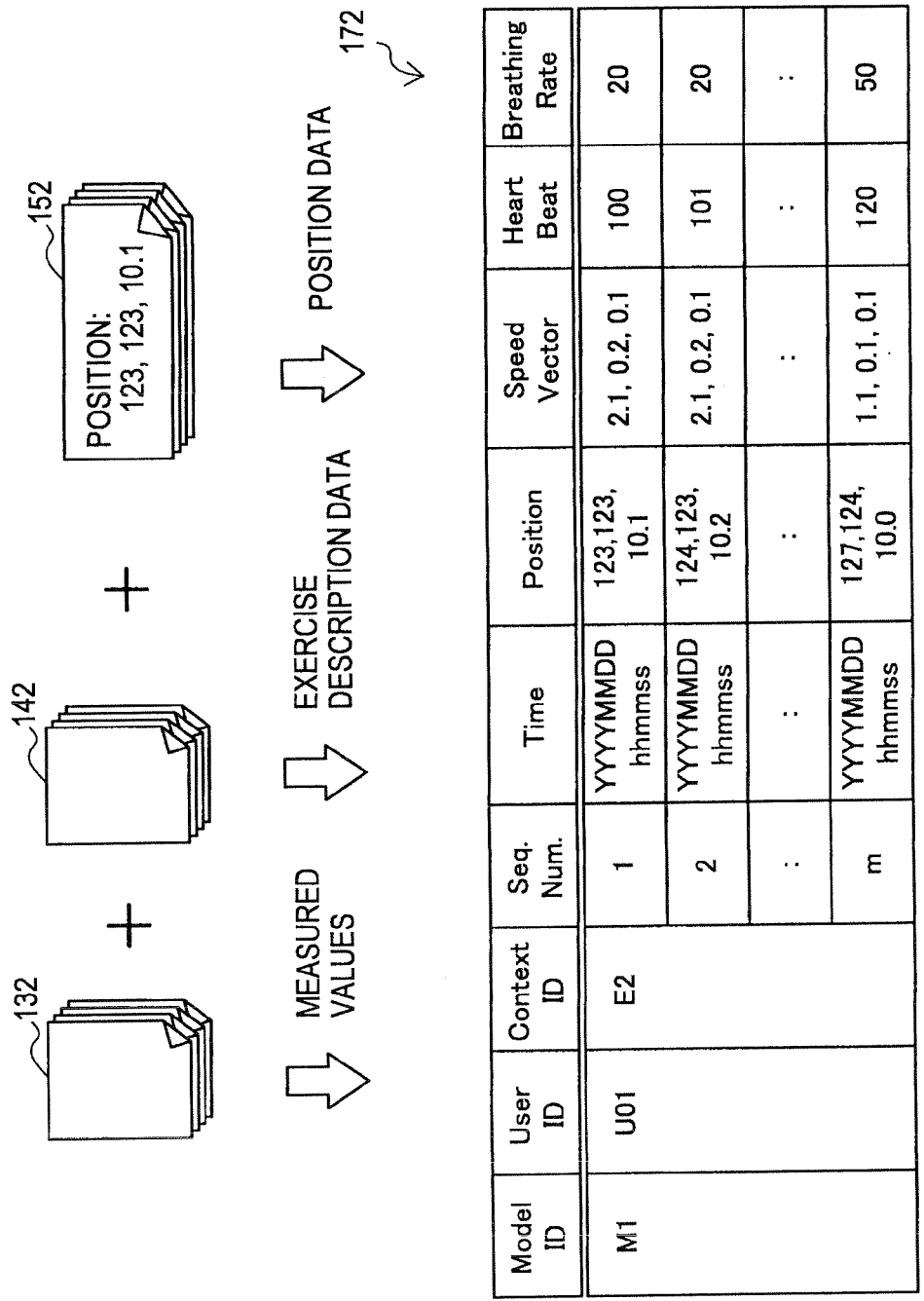
FIG. 7 is an explanatory view to explain creation of an exercise model according to one embodiment.

FIG. 7 is an explanatory view to explain creation of an exercise model according to the embodiment. The measured data 132, the exercise description data 142 and the position data 152 which are stored in time series in the storage unit 160 are shown at the top of FIG. 7. In the example of FIG. 7, the position data 152 contains the latitude, longitude and altitude indicating the current position of a user which are acquired by the GPS function. The model creation unit 170 specifies a series of data corresponding to one (one set of) exercise of a user among those data and assigns one model ID for identifying an exercise model, for example. Further, the model creation unit 170 assigns a sequence number (Seq. Num) to each time stamp of the specified series of data. Then, the model creation unit 170 associates data to be used for creation of an output image with each time stamp. In the example of FIG. 7, the values of time stamp, position, speed vector, heart beat and breathing rate are associated with each sequence number. Further, the model creation unit 170 associates those data with the exercise description data (which is the context ID in the example of FIG. 7). Although one representative context ID ("E2") is associated with one model ID ("M1") in the example of FIG. 7, the context ID may be associated one by one with the sequence number. The model creation unit 170 outputs the exercise model 172 created in this manner to the storage unit 160.

The storage unit 160 accumulates one or more exercise models created by the model creation unit 170 by using storage medium. The exercise models accumulated in the storage unit 160 are then selectively output from the storage unit 160 at the time of displaying the exercise model, which is described in the following section.

[2-4. Display of Exercise Model]

(2-4-1 Selection of Model to be Displayed)

In this embodiment, a user of the information processing system 1 can select either one of model creation mode or model display mode at the time of doing exercise. When a user selects the model creation mode, the information processing device 100 performs the measurement and recognition of exercise and the creation of exercise model, which are described above. On the other hand, when a user selects the model display mode, the information processing device 100 performs display of exercise model, which is described in this section. The display of exercise model mainly involves the storage unit 160, the selection unit 180 and the output unit 190. Note that the above-described measurement and recognition of exercise can be performed in parallel during the display of exercise model.

The selection unit 180 selects one or more exercise models to be displayed for a user doing exercise from the plurality of exercise models stored in the storage unit 160 according to a condition designated by the user or the system. The condition for selecting an exercise model is classified into a pre-condition designated before the start of exercise and a post-condition designated after the start of exercise. For example, the type of a person, the attribute of a person, the type of exercise, the range of a measured value, the created time of an exercise model or the like may be designated as the pre-condition.

Figure 8:
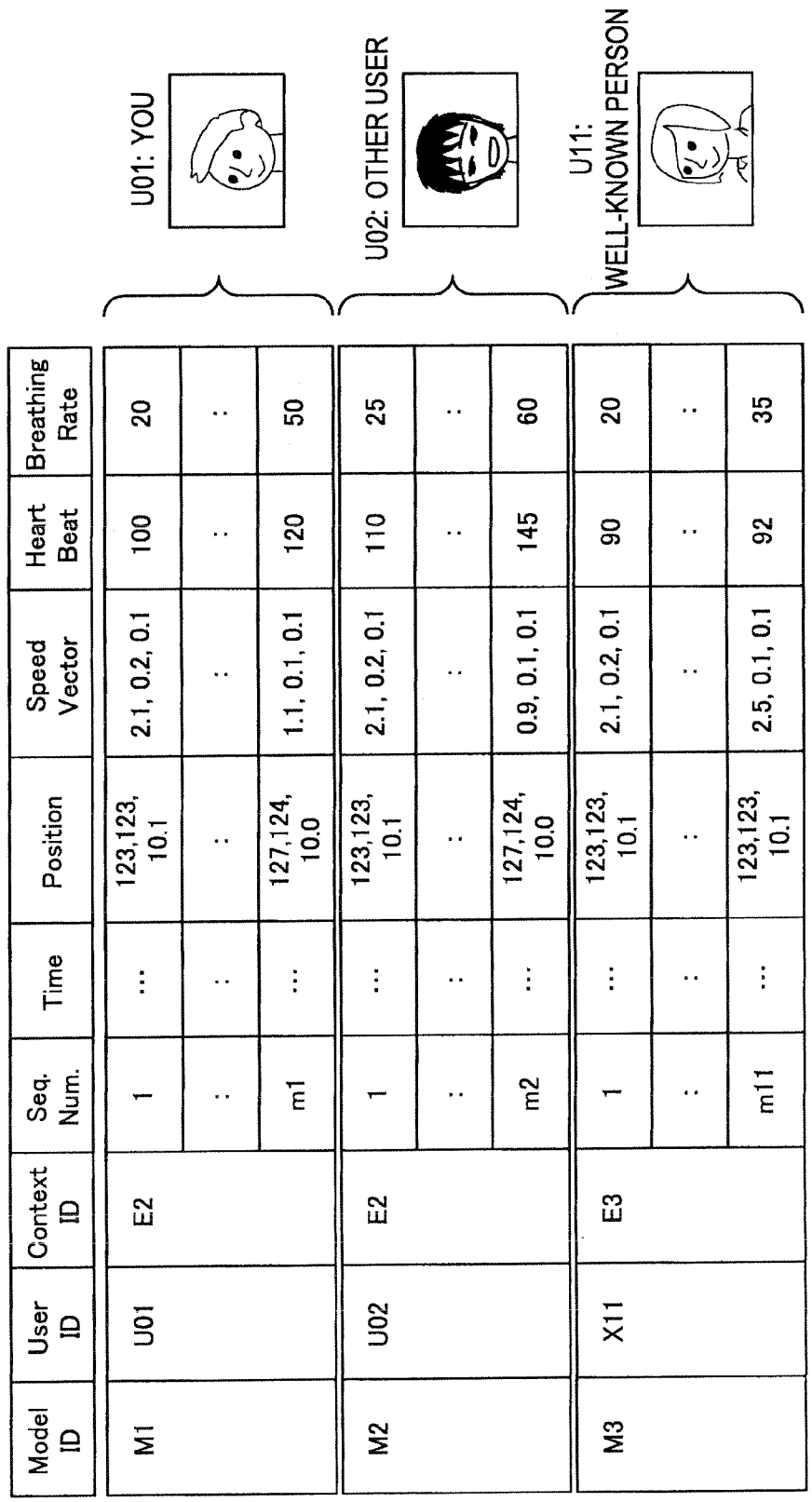
FIG. 8 is an explanatory view to explain a type of a person regarding an exercise model according to one embodiment.

FIG. 8 is an explanatory view to explain a type of a person regarding an exercise model according to one embodiment. Referring to FIG. 8, three exercise models accumulated by the storage unit 160 are shown. The exercise model with the model ID "M1" is referred to as an exercise model M1, the exercise model with the model ID "M2" is referred to as an exercise model M2, and the exercise model with the model ID "M3" is referred to as an exercise model M3. Further, it is assumed that a user U01 intends to use the information processing system 1 at the selection of the exercise model.

In the example of FIG. 8, the exercise model M1 is an exercise model that models exercise by the user U01. Thus, for the user U01 who intends to use the information processing system 1, the exercise model M1 is an exercise model for the past exercise of him/herself. On the other hand, the exercise model M2 is an exercise model that models exercise by a user U02. For the user U01, the exercise model M2 is an exercise model for exercise of another use. Further, the user ID of the exercise model M3 is "X11". This user ID indicates a well-known athlete such as a marathon runner, for example. The exercise model M3 for such a well-known athlete provides the model of exercise which many users target on, for example. In this manner, from the viewpoint of a user who intends to use the information processing system 1, each exercise model may be classified into three kinds of types, the exercise model of oneself, the exercise model of another user, and the exercise model of a well-known person. In this embodiment, the selection unit 180 selects a specific type of exercise model designated by a user among the plurality of types as the exercise model to be displayed.

FIG. 9 is an explanatory view to explain a selection condition designation screen provided to a user by the selection unit 180 according to the embodiment. Referring to FIG. 9, a selection condition designation screen W2 as an example is shown. The selection condition designation screen W2 includes a model number designation field F21, a target period designation field F22, a type designation field F23, and an additional condition designation field F24. The model number designation field F21 is a field for designating the maximum value of the number of exercise models to be displayed at the same time. The target period designation field F22 is a field for designating the created time of the exercise model to be selected.

The type designation field F23 is a field for designating a type of a person of the exercise model to be selected. For example, when "you" is designated as the type of a person, the selection unit 180 selects the exercise model created in the past for the same person as the user doing exercise.

Further, when "other user" is designated as the type of a person, the selection unit 180 selects the exercise model created in the past for a user different from the user doing exercise. At this time, it is preferred that the selection unit 180 preferentially selects the exercise model for another user having the attribute designated in the additional condition designation field F24 being common or similar to a user doing exercise, for example. For example, when "age" is designated in the additional condition designation field F24, the exercise model for a user of near age can be preferentially selected. Further, the attribute which can be designated in the additional condition designation field F24 may include at least one of age, sex, height and weight, for example.

Furthermore, when "well-known person" is designated as the type of a person, the selection unit 180 selects the exercise model for "well-known person". Further, as shown in FIG. 9, the name of a specific well-known person (e.g. "person A"), not "well-known person", may be designated as the type of a person.

In addition, although not shown in FIG. 9, the type of exercise (e.g. any or walking, running and swimming), the range of measured value (e.g. 3 to 5 [km] as the total distance of running) designated by the exercise description data of the exercise model or the like may be designated as the pre-condition.

As the post-condition, a condition according to the measured value measured in parallel with the display of exercise model, the current position of a user, the type of exercise recognized in parallel with the display of exercise model or the like may be used. For example, after a user starts exercise, the selection unit 180 may select the exercise model for the same type of exercise as the type of exercise recognized by the exercise recognition unit 140. Further, when there are a plurality of candidates for the exercise model to be selected, the selection unit 180 may select the exercise model with the measured values such as heart beat or breathing rate being closer to the current measured values of the user, for example. Furthermore, the selection unit 180 may select the exercise model for exercise done in the position close to the current position of the user, for example.

In addition, when the current exercise of the user recognized by the exercise recognition unit 140 is different from exercise specified by the exercise description data of the exercise model being processed by the output unit 190, the selection unit 180 selects another exercise model to be processed by the output unit 190. For example, in the case where the exercise model selected according to the pre-condition only for the type of person is "walking" model, when the current exercise of the user recognized by the exercise recognition unit 140 has changed to "running", the selection unit 180 newly selects "running" model. The model to act as an appropriate comparison target for exercise of the user can be thereby dynamically displayed.

(2-4-2 Display of Selected Model)

The output unit 190 creates a series of output images that represent the measured values contained in the exercise model and the exercise specified by the exercise description data in time series for the exercise model selected by the selection unit 180. The output unit 190 then outputs the created output images to the display device 104.

In this embodiment, the output image created by the output unit 190 is an image that displays a character as an avatar of a person doing the exercise specified by the exercise description data. Specifically, if the exercise specified by the exercise description data is running (context ID=E2 ("Running") as in the exercise model M1 shown in FIG. 7, for example, the output unit 190 creates the output image displaying the running character.

Figure 10:
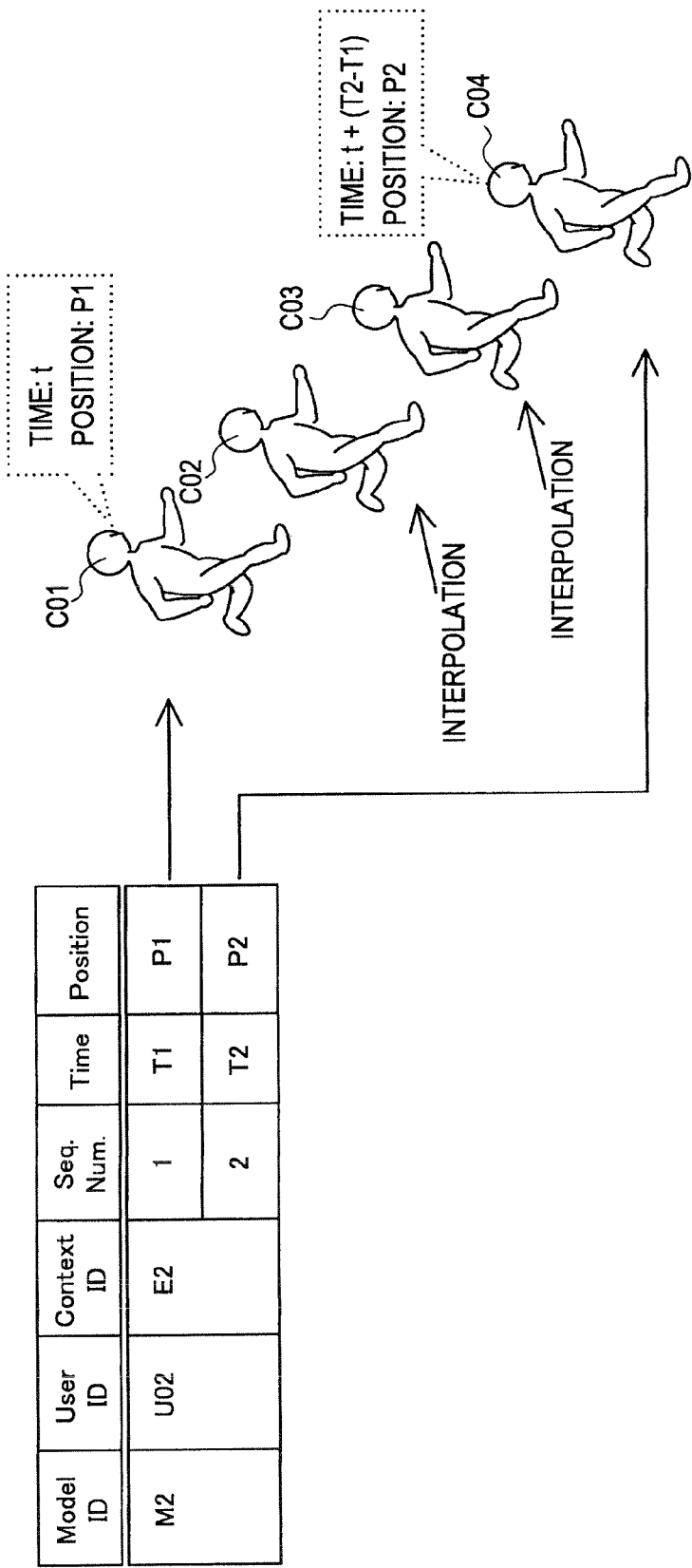
FIG. 10 is a first explanatory view to explain creation of a character image according to one embodiment.

FIG. 10 is a first explanatory view to explain creation of a character image by the output unit 190 according to the embodiment.

Referring to FIG. 10, a character image C01 at time t is created according to the time stamp T1 and the position P1 corresponding to the sequence number #1 of the exercise model M2 shown at the left. Further, a character image C04 at time t+(T2−T1) is created according to the time stamp T2 and the position P2 corresponding to the sequence number #2 of the exercise model M2. Furthermore, as character images at time points between the time t and the time t+(T2−T1), two character images C02 and C03 are created, in this manner, the output unit 190 not only creates the character images corresponding to the time-series data contained in the exercise model but also interpolates the character images at time points between the two successive data thereby creating a series of character images (i.e. video) serving as an avatar of a person moving along the time axis.

Note that the output unit 190 may vary the body shape, costume or the like of such a character image depending on the attributes of the corresponding person such as age, sex, height and weight, or the type of the corresponding person. Further, the face picture of a user registered as user data may be displayed at the head of the character image. This allows a user to more easily recognize by intuition which person each character represents.

Further, in this embodiment, the output unit 190 varies the display position or the size of the character in a time-series manner according to the position of a person indicated by the position data of the selected exercise model and the current position of a user.

Figure 11:
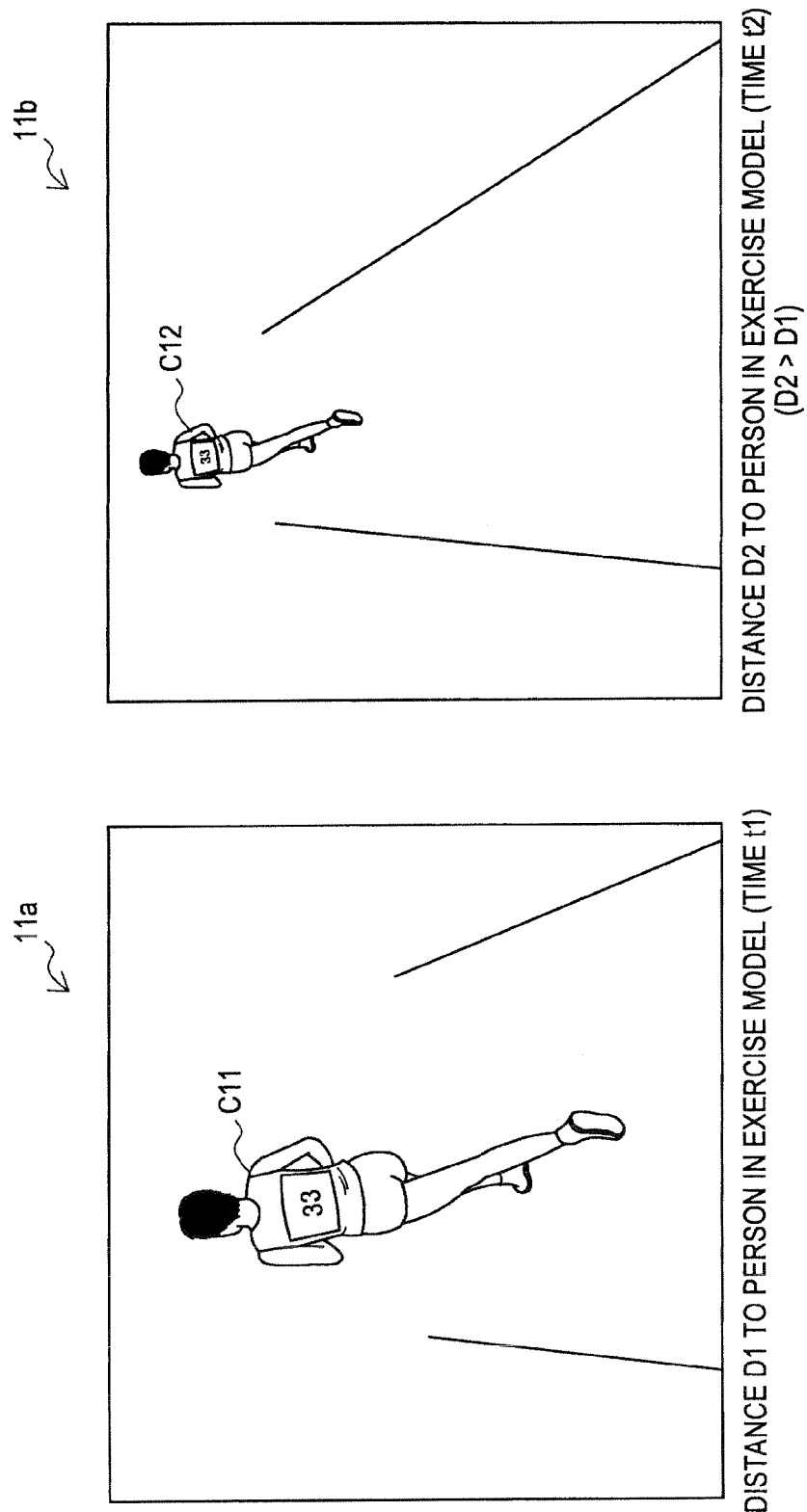
FIG. 11 is a second explanatory view to explain creation of a character image according to one embodiment.

FIG. 11 is a second explanatory view to explain creation of a character image by the output unit 190 according to the embodiment.

A character image C11 generated at time t1 is shown at the left of FIG. 11 (cf. FIG. 11*a*). In the information processing system 1 illustrated in FIG. 1, for example, the display position of the character image C11 may be determined based on the position of a person at time t1 of the selected exercise model, the current position of a user, and the orientation (direction) of a user's line of sight which is detected by a direction sensor mounted on the display device 104*a*. In this case, when a user looks forward, the user can view a person ahead of him/her. Further, when a user looks back, the user can view a person behind him/her. Further, in the information processing system 1*b* illustrated in FIG. 2, the display position of the character image C11 may be determined based on the position of a person at time t1 in the virtual space and the current position of a user, for example. Furthermore, in the information processing system 1*c* illustrated in FIG. 3, the display position of the character image C11 may be determined based only on the position of a person at time t1 of the selected exercise model, for example (in this case, a swimming character is displayed instead of a running character).

Further, the size of the character image C11 is determined according to the position of a person indicated by the position data of the selected exercise model and the current position of a user. For example, it is assumed that the distance between the person displayed at time t1 and the user is D1, and the distance between the person displayed at time t2 and the user is D2. Because D2>D1, the character image C11 displayed at time t1 (cf. FIG. 11*a*) is larger than the character image C12 displayed at time t2 (cf. FIG. 11*b*).

By looking at such images, the user can recognize by intuition the status of exercise of him/herself in the past, another user or a well-known person as a target of comparison while doing exercise. For example, the feeling of distance sensed by the above-described output image indicates a difference in the amount of exercise or the level of exercise between the current exercise of the user and the model.

Further, the output unit 190 may vary the state of the character image in time series according to the measured values contained in the selected exercise model. For example, it is assumed that the exercise model contains the measured values about heart beat and breathing rate. In this case, it can be considered that, as the values of heart beat and breathing rate are greater, a person associated with the exercise model felt more fatigue at the point of time. In light of this, the output unit 190 may vary the state of the character image in time series according to the level of fatigue estimated from the values of heart beat and breathing rate, for example. Further, the output unit 190 may vary the state of the character image according to the speed, body temperature, or other kinds of measured values contained in the exercise model, for example.

Figure 12:
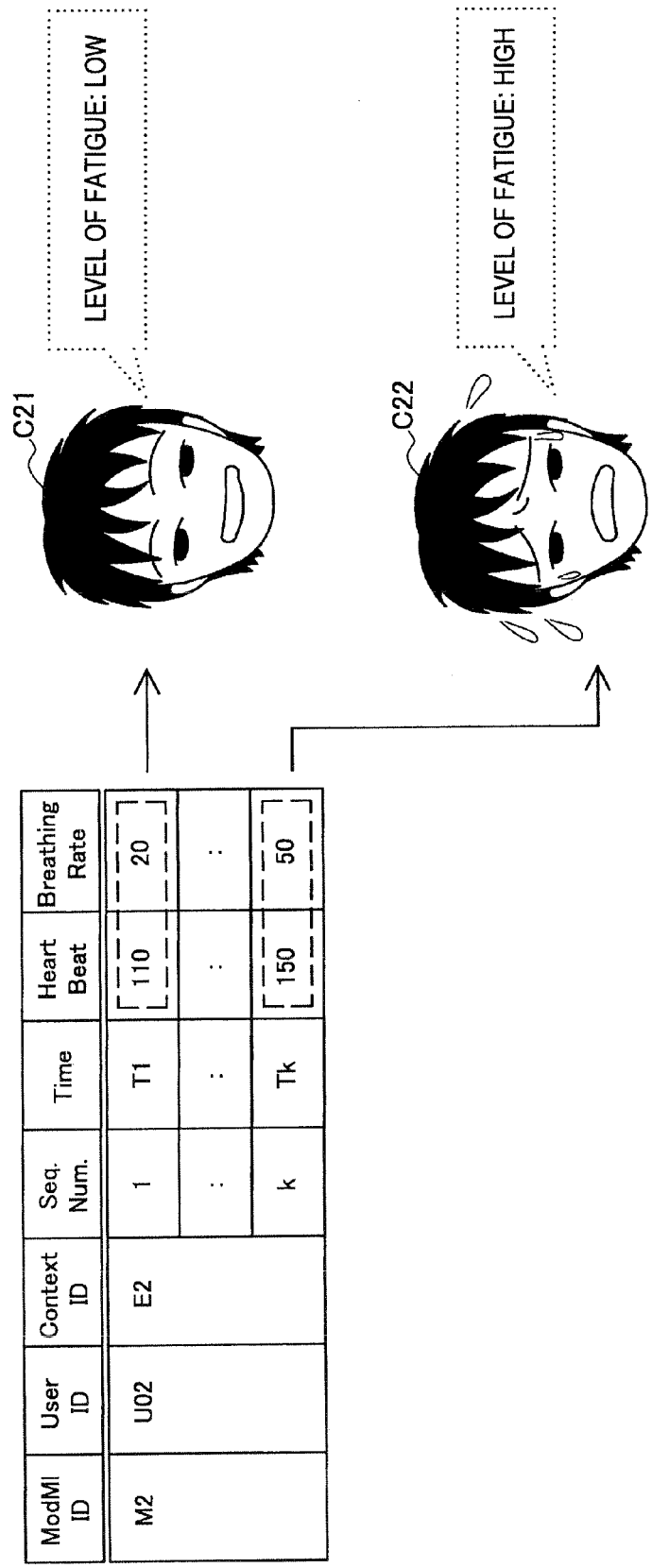
FIG. 12 is a third explanatory view to explain creation of a character image according to one embodiment.

FIG. 12 is a third explanatory view to explain creation of a character image by the output unit 190 according to the embodiment.

Referring to FIG. 12, at the time point of the sequence number #1 of the exercise model M2, the heart beat of the user U02 is 110, and the breathing rate is 20. On the other hand, at the time point of the sequence number #k of the exercise model M2, the heart beat of the user U02 is 150, and the breathing rate is 50. Therefore, it is estimated that the level of fatigue of the user U02 at the time point of the sequence number #k was relatively higher than the level of fatigue of the user U02 at the time point of the sequence number #1. Thus, the output unit 190 adds animation of sweat dropping which represents the fatigue to the character image C22 at the time point of the sequence number #k, for example. Note that, instead of such animation, the state of the character (the state of the person in the exercise model) may be represented using the color of the character image, the text or indicator associated with the character image or the like.

In this embodiment, the output unit 190 displays information for displaying at least one kind of measured value in the exercise model and information for displaying the current measured value for the user in the output image, in addition to the character image as described above.

(2-4-3 Example of Output Image)

Figure 13:
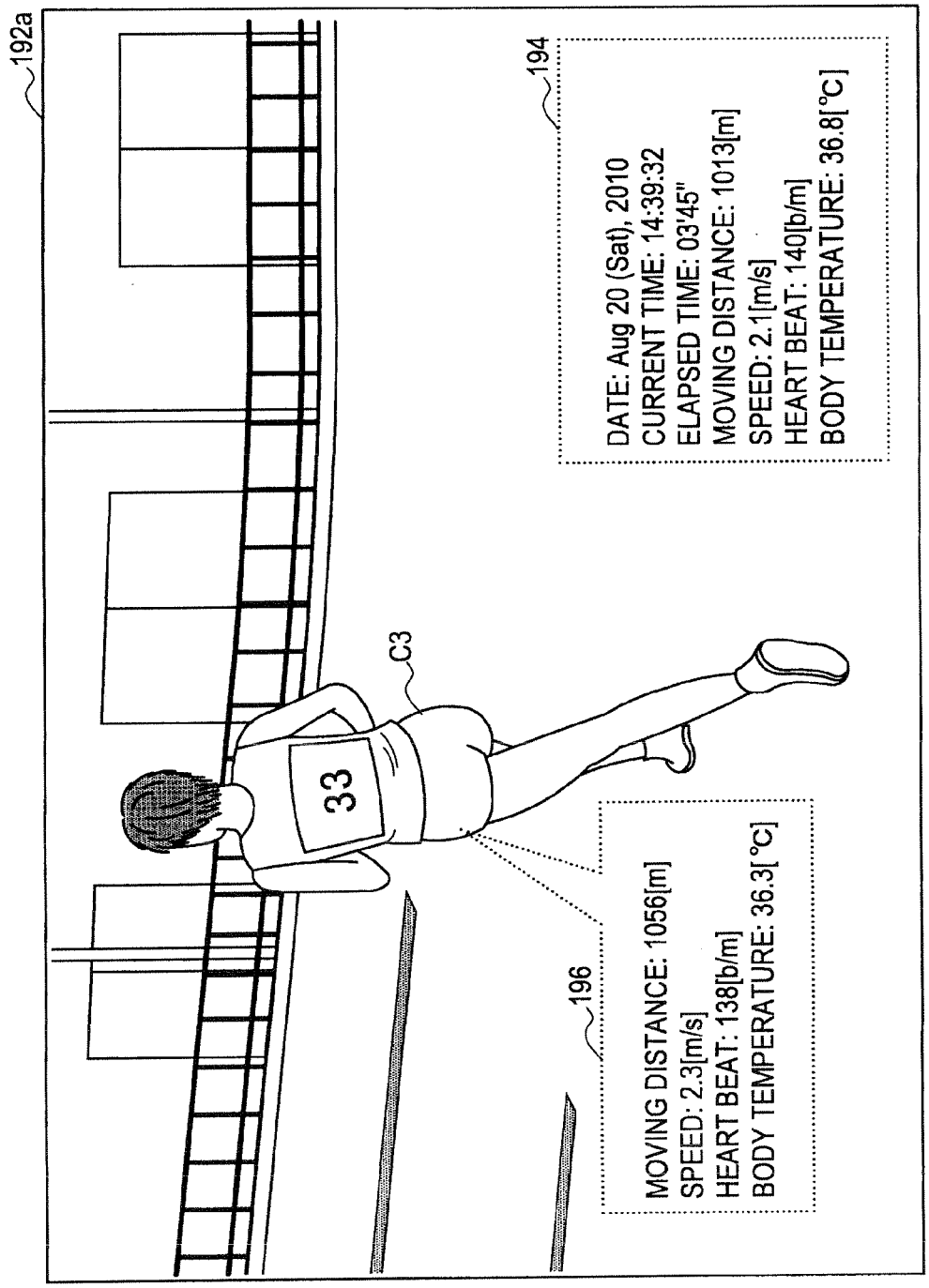
FIG. 13 is an explanatory view showing an example of an output image according to one embodiment.
Figure 14:
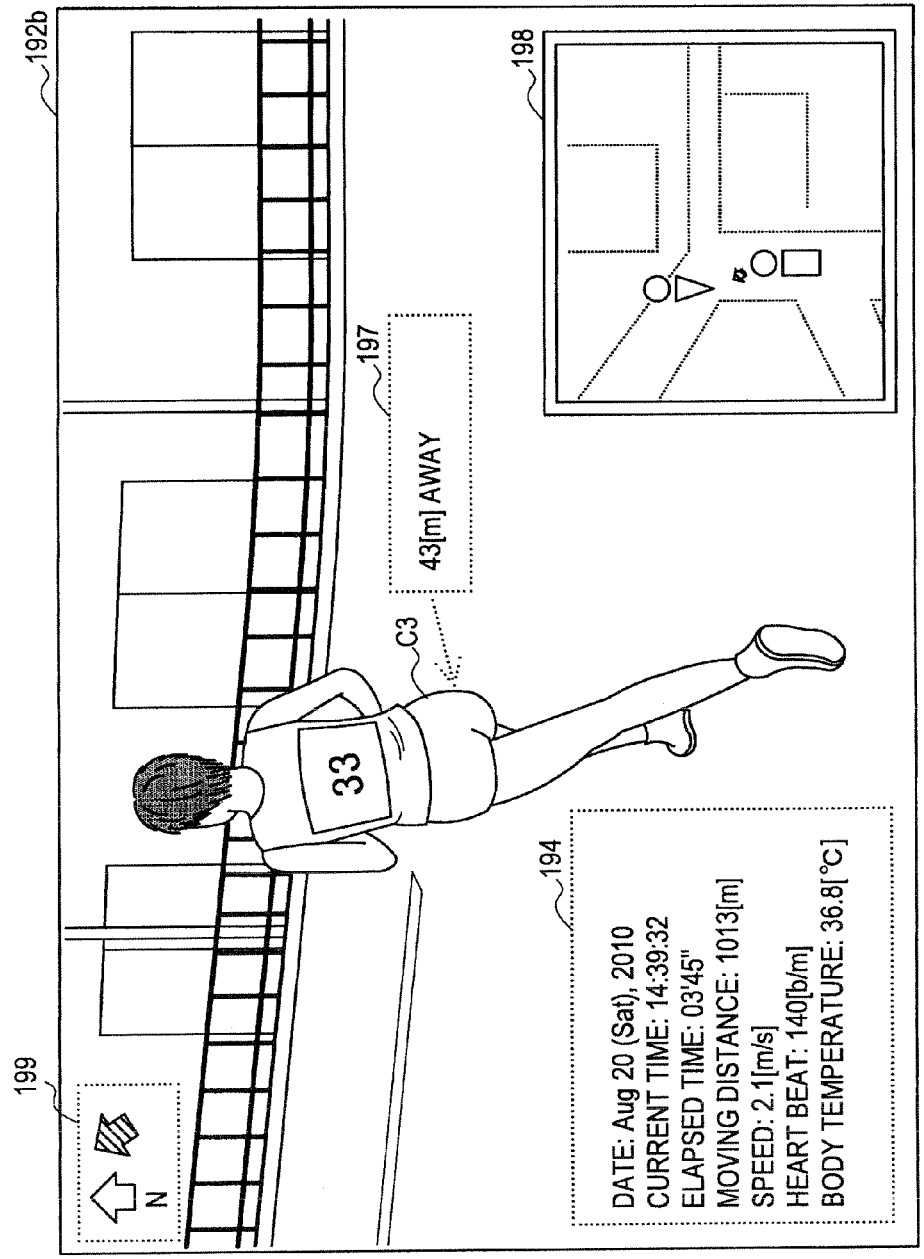
FIG. 14 is an explanatory view showing another example of an output image according to one embodiment.

FIGS. 13 and 14 are explanatory views respectively showing an example of an output image according to the embodiment.

Referring to FIG. 13, an output image 192*a* is shown as an example. The output image 192*a* includes a character image C3, user information 194, and model information 196. The character image C3 is an image of a character as an avatar of a person corresponding to the exercise model selected by the selection unit 180. The user information 194 indicates measured values such as the moving distance of a user from the start of exercise, the user's current speed, heart beat and breathing rate in addition to general information such as the date, current time and elapsed time from the start of exercise and so on. On the other hand, the model information 196 indicates measured values such as the moving distance of a person serving as a model from the start of exercise, the person's current speed, heart beat and breathing rate.

Referring to FIG. 14, an output image 192*b* is shown as another example. The output image 192*b* includes a character image C3, user information 194, additional information 197, map information 198, and bearing information 199. The additional information 197 indicates supplementary information such as the current distance between a person serving as a model and a user. The map information 198 indicates the position of a person serving as a model and the current position of a user on a map. The bearing information 199 indicates the direction of movement of a user recognized from a speed vector and the direction of the line of sight of a user acquired by a direction sensor mounted on the display device 104*a*. By checking the additional information 197, the map information 198 and the bearing information 199, a user can grasp a difference between the current state of him/herself and the state of a person serving as a model more easily while doing exercise.

3. FLOW OF PROCESS ACCORDING TO EMBODIMENT

[3-1. Overall Flow]

Figure 15:
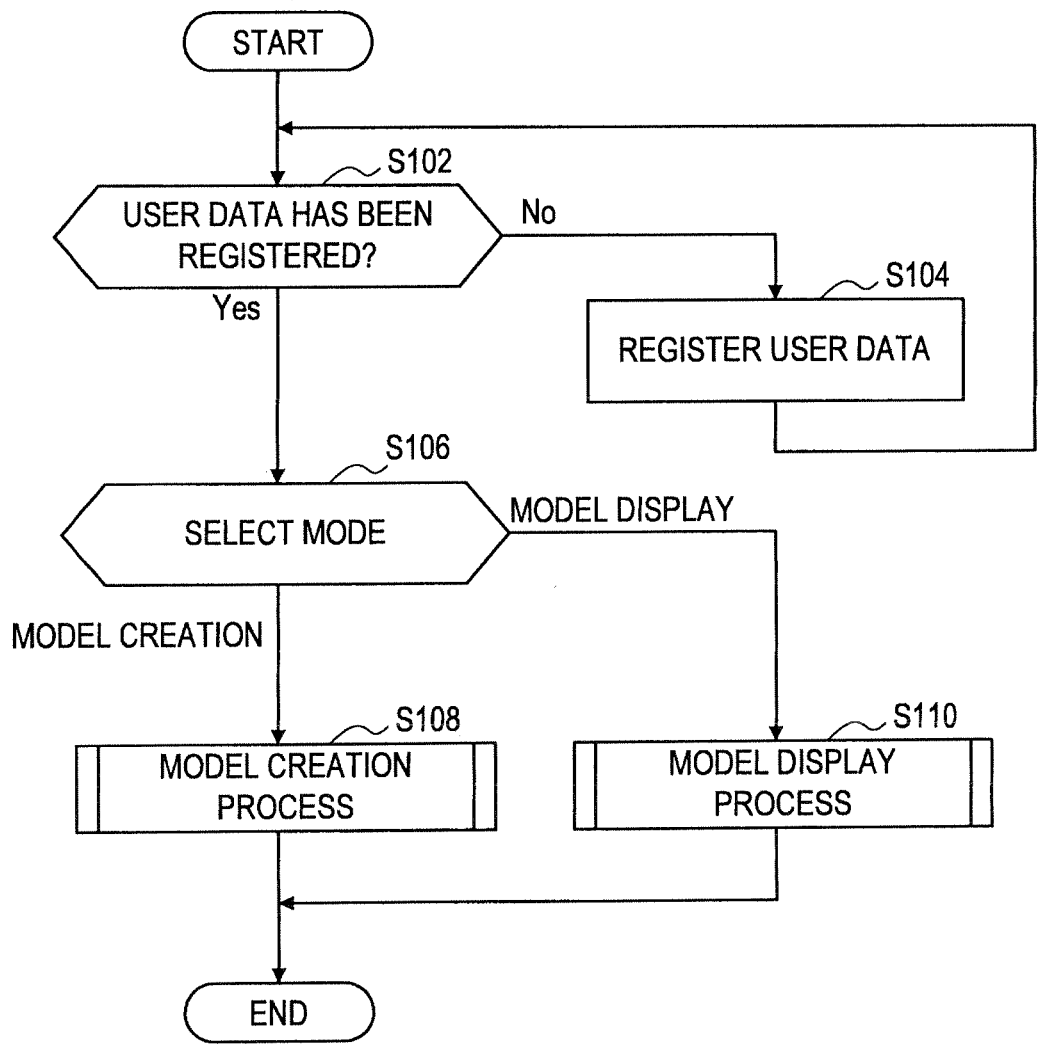
FIG. 15 is a flowchart showing an example of an overall flow of information processing according to one embodiment.

FIG. 15 is a flowchart showing an example of an overall flow of information processing according to the embodiment. The flowchart of FIG. 15 shows the overall flow of processing from the start of use to the end of use of the information processing system 1.

First, the user data management unit 120 determines whether use data has been registered or not (step S102). When user data has not been registered, the user data management unit 120 presents the registration screen W1 as illustrated in FIG. 5 to a user and accepts registration of user data (step S104). The process then proceeds to step S106.

Then, a user selects either one of the model creation mode or the model display mode (step S106). When the model creation mode is selected, the process proceeds to step S108 and performs the model creation process. On the other hand, when the model display mode is selected, the process proceeds to step S110 and performs the model display process.

[3-2. Model Creation Process]

Figure 16:
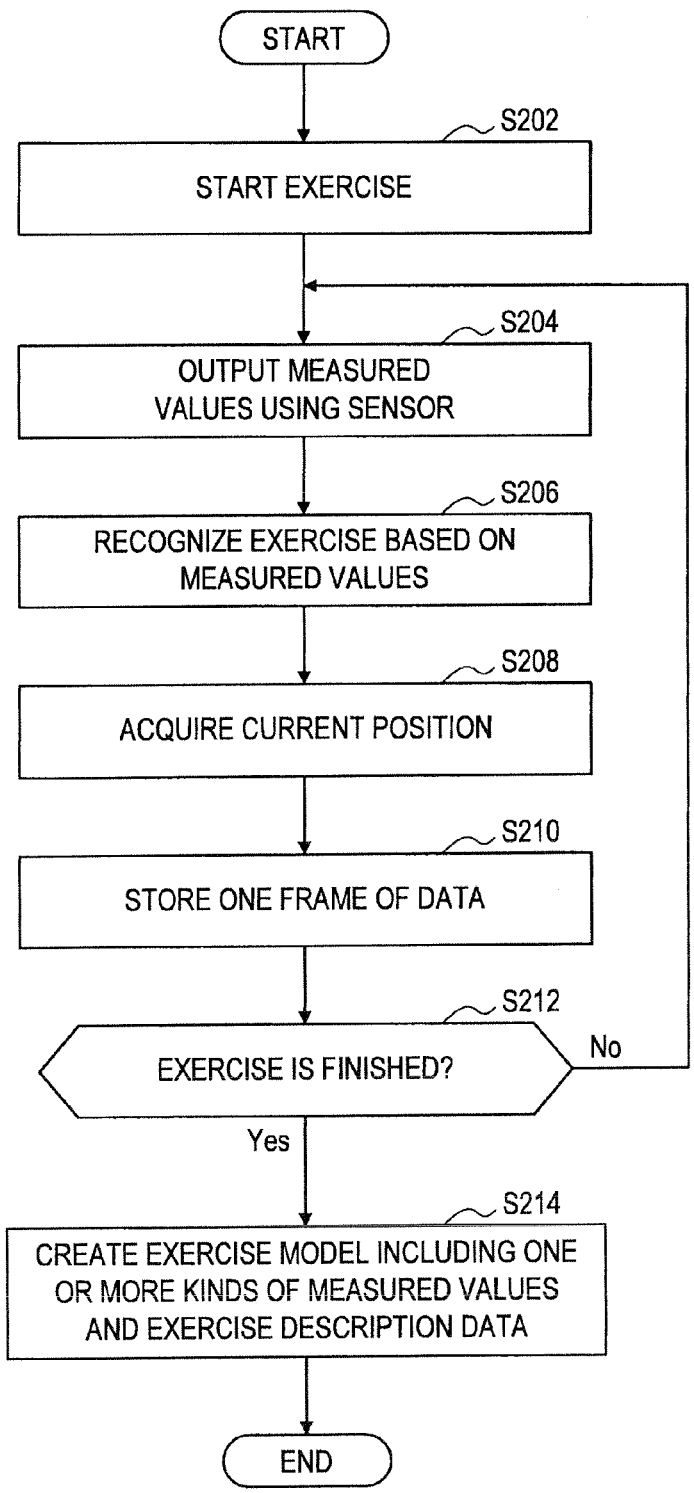
FIG. 16 is a flowchart showing an example of a flow of a model creation process according to one embodiment.

FIG. 16 is a flowchart showing an example of a flow of the model creation process according to the embodiment. In the following, the case where the model creation process is performed at the point of time when a series of exercises by a user are finished is described by way of illustration.

Referring to FIG. 16, exercise by a user is started (step S202). After that, the processing from step S204 to step S212 is repeated at a certain period, such as several times in one second or once in several seconds, for example, during exercise by the user.

First, the measurement unit 130 measures one or more kinds of parameters for a user doing exercise with use of the sensor set 102 and outputs measured values as a result of the measurement (step S204). Then, the exercise recognition unit 140 recognizes the user's exercise based on the measured values output from the measurement unit 130 (step S206). The position acquisition unit 150 then acquires the user's current position (step S208). Then, the storage unit 160 stores one frame of data which contains exercise description data and position data (step S210).

After that, when exercise by the user continues, the process returns to the step S204. On the other hand, when exercise by the user is finished, the process proceeds to step S214 (step S212).

In the step S214, the model creation unit 170 creates the exercise model which includes one or more kinds of measured values contained in the measured data and exercise description data as a result of recognition by the exercise recognition unit 140 described above (step S214).

[3-3. Model Display Process]

Figure 17:
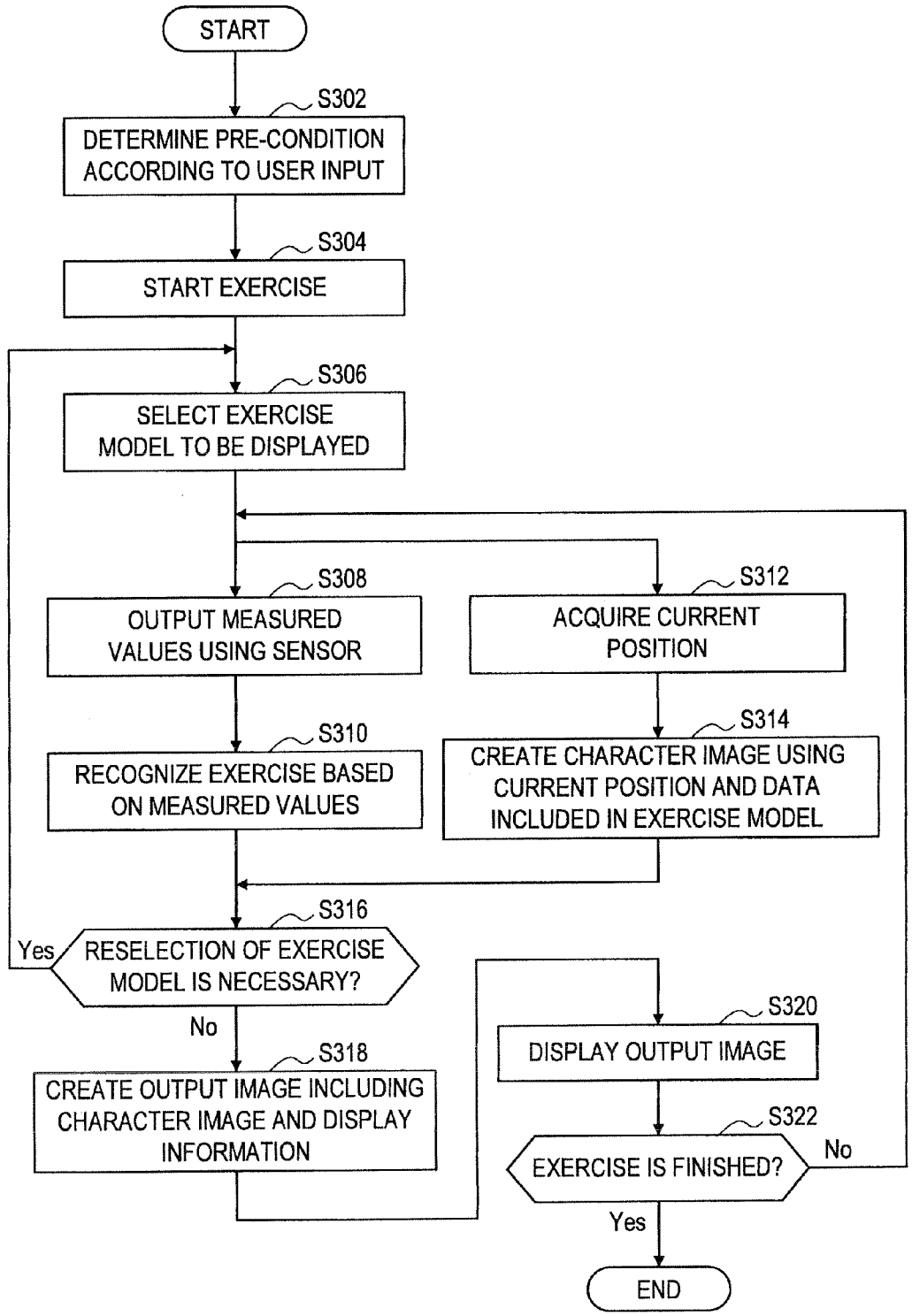
FIG. 17 is a flowchart showing an example of a flow of a model display process according to one embodiment.

FIG. 17 is a flowchart showing an example of a flow of the model display process according to the embodiment.

Referring to FIG. 17, the selection unit 180 determines a pre-condition in response to a user input to the selection condition designation screen W2 illustrated in FIG. 9, for example (step S302). Then, exercise by a user is started (step S304). After that, the processing from step S306 to step S322 is repeated at a certain period, such as several times in one second or once in several seconds, for example, during exercise by the user.

First, the selection unit 180 selects one or more exercise models to be displayed for the user doing exercise from a plurality of exercise models stored in the storage unit 160 (step S306). Next, the measurement unit 130 measures one or more kinds of parameters for the user doing exercise with use of the sensor set 102 and outputs measured values as a result of the measurement (step S308). Then, the exercise recognition unit 140 recognizes the user's exercise based on the measured values output from the measurement unit 130 (step S310). The position acquisition unit 150 then acquires the user's current position (step S312). The output unit 190 then creates a character image using the user's current position and the measured values, the exercise description data and the position data included in the exercise model (step S314).

Then, the selection unit 180 determines whether reselection of the exercise model is necessary or not by comparing the type of exercise of the exercise model selected in the step S306 and the type of exercise of the user recognized in the step S310 (step S316). When reselection of the exercise model is necessary, the process returns to the step S306, and reselection of the exercise model using a post-condition is performed. On the other hand, when reselection of the exercise model is not necessary, the process proceeds to step S318.

In the step S318, the output unit 190 creates an output image including a character image and display information (e.g. the user information 194 and the model information 196 illustrated in FIG. 13) (step S318). Then, the output unit 190 displays the created output image with use of the display device 104 (step S320).

After that, when exercise by the user continues, the process returns to the steps S308 and S312. On the other hand, when exercise by the user is finished, the model display process ends. Note that, in parallel with the model display process shown in FIG. 17, the storing of data in the step S210 shown in FIG. 16 may be performed, and further the creation of the exercise model in the step S214 may be performed after exercise by the user is finished.

4. SUMMARY

Embodiments of the present invention are described above with reference to FIGS. 1 to 17. According to an embodiment, in the information processing device 100, a plurality of exercise models, each of which includes one or more kinds of measured values measured in time series for a person doing exercise and exercise description data specifying exercise recognized based on the measured values, are stored in advance. Then, a series of output images that represent the measured values and the exercise specified by the exercise description data in time series for the exercise model selected according to a designated condition are output to be visible to the user doing exercise. The user can thereby easily recognize the type of exercise and the status of exercise in time series for the exercise model to be compared with.

Further, according to this embodiment, the output image displayed for a user is an image that displays a character as an avatar of a person doing exercise specified by the exercise description data. Displaying such a character in the output image brings out the user's desire to compete to thereby maintain or enhance the motivation for exercise. Particularly, in this embodiment, the display position or the size of the character varies according to the position of a person included in the exercise model and the current position of a user. A user can thereby easily grasp whether the user is ahead of or behind the person serving as a model and the extent that the user is ahead of or behind the person. This enables intuitive comparison between the exercise of the user and the exercise of the person serving as a model, and it is expected to further enhance the user's motivation.

Further, according to this embodiment, a user can select an exercise model for the past exercise of him/herself among a plurality of exercise models. Furthermore, a user can also select an exercise model for a well-known person whom the user targets on, for example, among a plurality of exercise models. In addition, a user can select an exercise model for another user with similar attributes such as age and sex among a plurality of exercise models. With such various options provided, a user can flexibly make comparison about exercise according to the purpose.

Further, a according to this embodiment, the sense of game upon exercise, such as competition with a person serving as a model, is offered to a user. Further, comparison with the exercise model for a user in the ideal state in the past, another person or a well-known person, for example, enables effective learning of the pace of exercise or the like, and improvement of exercise capacity of a user can be also expected.

The series of processes by the information processing device 100 described in this specification is typically implemented using software. A program composing the software that implements the series of processes may be prestored in a storage medium mounted internally or externally to the information processing device 100, for example. Then, each program is read into RAM (Random Access Memory) of the information processing device 100 and executed by a processor such as CPU (Central Processing Unit).

Although preferred embodiments of the present invention are described in detail above with reference to the appended drawings, the present invention is not limited thereto. It should be understood by those skilled in the art that various modifications, combinations, sub-combinations and alterations may occur depending on design requirements and other factors insofar as they are within the scope of the appended claims or the equivalents thereof.

The present application contains subject matter related to that disclosed in Japanese Priority Patent Application JP 2010-078892 filed in the Japan Patent Office on Mar. 30, 2010, the entire content of which is hereby incorporated by reference.

What is claimed is:

1. An information processing device comprising:
   a storage unit configured to store a plurality of exercise models, each exercise model of the plurality of exercise models including values in time series and exercise description data specifying an exercise identified based on the values;
   a selection unit configured to select at least one exercise model from the plurality of exercise models according to a condition, wherein the at least one selected exercise model comprises first values from the values and first exercise description data from the exercise description data, the first exercise description data specifying a first exercise identified based on the first values; and
   an output unit configured to output a comparison display comprising a series of output images representing, as an avatar, the first values and the first exercise specified by the first exercise description data in time series for the at least one selected exercise model selected by the selection unit and information representing second values corresponding to the person currently doing the first exercise, wherein
   the at least one selected exercise model includes position data indicating a position of a previously-recorded person doing the first exercise,
   the information processing device further includes a position acquisition unit configured to acquire a current position of the person currently doing the first exercise, and
   the output unit is further configured to modify a size of the avatar in time series according to a distance between the position of the previously-recorded person indicated by the position data of the at least one selected exercise model and the current position of the person currently doing the first exercise.

2. The information processing device according to claim 1, wherein:
   the output unit is configured to modify a state of the representation in time series according to the first values in the at least one selected exercise model.

3. The information processing device according to claim 1, wherein:
   the output images comprise an image further displaying at least one kind of the values.

4. The information processing device according to claim 1, wherein:
   the condition for selecting an exercise model comprises exercise models wherein the person currently doing the first exercise is performing a different exercise; and
   the output unit is further configured to output the series of the output images representing the first values comprising at least one first parameter associated with performance of the first exercise by the user along with at least one image representing at least one second parameter associated with performance of the second exercise by the user.

5. The information processing device according to claim 1, wherein:
   the condition for selecting an exercise model comprises exercise models that are based on recorded values of a well-known person performing an exercise.

6. The information processing device according to claim 1, wherein:
   the condition for selecting an exercise model comprises exercise models that are based on at least one attribute of an associated second user being common or similar to at least one attribute of a user doing an exercise, the at least one attribute comprising an attribute selected from the following: age, sex, height and weight.

7. The information processing device according to claim 1, further comprising:
   a measurement unit that is configured to output measured values for a user currently doing a second exercise; and
   an exercise recognition unit that is configured to identify the second exercise of the user based on the measured values output by the measurement unit, wherein:
   when the second exercise currently performed by the user and identified by the exercise recognition unit is different from the first exercise specified by the first exercise description data of the at least one selected exercise model being processed by the output unit, the selection unit is configured to select another exercise model of the plurality of exercise models to be processed by the output unit.

8. The information processing device according to claim 1, further comprising:
   a measurement unit that is configured to output the values for a person doing an exercise;
   an exercise recognition unit that is configured to identify an exercise of the person based on the values output by the measurement unit; and
   an exercise model creation unit that is configured to create an exercise model for the person using a result of the identification of the exercise by the exercise recognition unit.

9. The information processing device according to claim 1, wherein the values are output from at least one sensor.

10. The information processing device according to claim 1, wherein:
the first values comprise at least one first parameter associated with performance of the first exercise by a person.

11. The information processing device according to claim 10, wherein:
the at least one first parameter comprises one or more parameters selected from the following: a heartbeat of the person, a breathing rate of the person, an acceleration of the person, a posture of parts of the body of the person, a speed of the person, a body temperature of the person and sweating of the person.

12. The information processing device according to claim 10, wherein:
the output unit is further configured to output at least one image representing at least one second parameter associated with performance of a second exercise by a user to allow a comparison of the at least one second parameter and the at least one first parameter of the first values in the at least one selected exercise model.

13. An image output method using an information processing device including a storage unit configured to store a plurality of exercise models, each exercise model of the plurality of exercise models including values in time series and exercise description data specifying an exercise identified based on the values, the method comprising:
selecting at least one exercise model from the plurality of exercise models according to a condition, wherein the at least one selected exercise model comprises first values from the values and first exercise description data from the exercise description data, the first exercise description data specifying a first exercise identified based on the first values;
outputting a comparison display comprising a series of output images representing, as an avatar, the first values and the first exercise specified by the first exercise description data in time series for the at least one selected exercise model; and information representing second values corresponding to the person currently doing the first exercise,
wherein:
the at least one selected exercise model includes position data indicating a position of a previously-recorded person doing the first exercise, and
the method further comprises acquiring a current position of the person currently doing the first exercise, and modifying a size of the avatar in time series according to a distance between the position of the previously-recorded person indicated by the position data of the at least one selected exercise model and the current position of the person currently doing the first exercise.

14. The image output method according to claim 13, wherein the first values comprise at least one first parameter associated with performance of the first exercise by a person, the method further comprising:
outputting at least one image representing at least one second parameter associated with performance of a second exercise by a user to allow a comparison between the at least one second parameter and the at least one first parameter of the first values in the at least one selected exercise model.

15. The image output method according to claim 14, wherein the condition for selecting an exercise model comprises a condition selected from the following: the same user as the user doing the second exercise, a well-known person, a person that is associated with at least one attribute that is common or similar to at least one attribute of the second user.

16. The image output method according to claim 13, further comprising:
acquiring measured values comprising at least one parameter associated with performance of a second exercise by a user;
identifying the second exercise based on the measured values; and
when the second exercise currently performed by the user is different from the first exercise specified by the first exercise description data of the at least one selected exercise model, selecting another exercise model of the plurality of exercise models comprising third values from the values and third exercise description data from the exercise description data, the third exercise description data specifying a third exercise identified based on the third values.

17. A program embodied on a non-transitory computer readable medium causing a computer that controls an information processing device including a storage unit configured to store a plurality of exercise models, each exercise model of the plurality of exercise models including values in time series and exercise description data specifying an exercise identified based on the values to implement:
a selection unit configured to select at least one exercise model from the plurality of exercise models according to a condition, wherein the at least one selected exercise model comprises first values from the values and first exercise description data from the exercise description data, the first exercise description data specifying a first exercise identified based on the first values; and
an output unit configured to output a comparison display comprising a series of output images representing, as an avatar, the first values and the first exercise specified by the first exercise description data in time series for the at least one selected exercise model selected by the selection unit and information representing second values corresponding to the person currently doing the first exercise, wherein:
the at least one selected exercise model includes position data indicating a position of a previously-recorded person doing the first exercise,
the information processing device further includes a position acquisition unit configured to acquire a current position of the person currently doing the first exercise, and
the output unit is further configured to modify a size of the avatar in time series according to a distance between the position of the previously-recorded person indicated by the position data of the at least one selected exercise model and the current position of the person currently doing the first exercise.

18. The program according to claim 17, wherein:
the first values comprise at least one first parameter associated with performance of the first exercise by a person; and
the output unit is further configured to output at least one image representing at least one second parameter associated with performance of a second exercise by a user to allow a comparison of the at least one second parameter and the at least one first parameter of the first values in the at least one selected exercise model.

19. A device comprising at least one processor and memory storing computer-executable instructions that, when executed by the at least one processor, perform a method comprising:
selecting at least one exercise model from a plurality of exercise models according to a condition, wherein:

each exercise model of the plurality of exercise models comprises values and exercise description data specifying an exercise identified based on the values; and the at least one exercise model comprises first values from the values and first exercise description data from the exercise description data, the first exercise description data specifying a first exercise identified based on the first values;

receiving second values acquired from a user doing a second exercise, wherein the second exercise is identified based on the second values; and generating a comparison display comprising images in time series representing, as an avatar, at least a portion of the first values and the first exercise specified for the at least one exercise model and information representing at least a portion of the second values and the second exercise, wherein:

the at least one selected exercise model includes position data indicating a position of a previously-recorded person doing the first exercise, and the method further comprises acquiring a current position of the person currently doing the second exercise, and modifying a size of the avatar in time series according to a distance between the position of the previously-recorded person indicated by the position data of the at least one selected exercise model and the current position of the person currently doing the second exercise.

20. The device according to claim 19, wherein the method further comprises:

displaying the output images on a display visible to the user while the user is doing the second exercise.

21. The device according to claim 19, wherein the method further comprises:

displaying the output images if a type of the second exercise is the same as a type of the first exercise; and if the second exercise currently performed by the user is different from the first exercise specified by the first exercise description data of the at least one exercise model, selecting an other exercise model of the plurality of exercise models and generating output images based on the other exercise model, the second images and the second exercise.

22. The device according to claim 19, further comprising:

a storage configured to store the plurality of exercise models.

23. The device according to claim 19, wherein the method further comprises:

generating the at least one exercise model by:

receiving the first values comprising at least one parameter associated with performance of the first exercise by a person;

identifying the first exercise based on the first values; and generating the at least one exercise model for the person based on the first identified exercise and the first values.

24. The device according to claim 23, wherein the person comprises the same user as the user doing the second exercise, another user, or a well-known person.

* * * * *